(12) United States Patent  (10) Patent No.: US 7,578,013 B2
Aikman  (45) Date of Patent: Aug. 25, 2009

(54) THERAPEUTIC POSITIONING DEVICE

(75) Inventor: Jonathan Aikman, Toronto (CA)

(73) Assignee: Somnaform Corporation (CA)

( * ) Notice: Subject to any disclaimer, the term of this patent is extended or adjusted under 35 U.S.C. 154(b) by 0 days.

(21) Appl. No.: 12/091,170

(22) PCT Filed: Oct. 25, 2006

(86) PCT No.: PCT/CA2006/001748

§ 371 (c)(1),
(2), (4) Date: Apr. 22, 2008

(87) PCT Pub. No.: WO2007/048236

PCT Pub. Date: May 3, 2007

(65) Prior Publication Data

US 2008/0222813 A1  Sep. 18, 2008

Related U.S. Application Data

(60) Provisional application No. 60/730,456, filed on Oct. 26, 2005.

(51) Int. Cl.
*A47G 9/00* (2006.01)
(52) U.S. Cl. ............... 5/632; 5/636; 5/641; 5/904; 5/922; 340/573.1; 600/300

(58) Field of Classification Search ............. 5/632, 5/630, 655, 636, 490, 944, 904, 641, 922; 600/300; 340/573.1
See application file for complete search history.

(56) References Cited

U.S. PATENT DOCUMENTS

| | | | |
|---|---|---|---|
| 4,901,384 A | 2/1990 | Eary | |
| 5,269,323 A | 12/1993 | Krouskop | |
| 5,727,267 A | 3/1998 | Keilhauer | |
| 5,987,674 A | 11/1999 | Schaffner et al. | |
| 6,052,848 A * | 4/2000 | Kelly | 5/632 |
| 6,499,164 B1 | 12/2002 | Leach | |
| 6,810,543 B2 * | 11/2004 | Fuhriman | 5/632 |
| 6,874,183 B1 | 4/2005 | Taylor | |
| 2007/0011812 A1 * | 1/2007 | Drucker | 5/636 |

* cited by examiner

*Primary Examiner*—Alexander Grosz
(74) *Attorney, Agent, or Firm*—David B. Tingey; Kirton & McConkie

(57) ABSTRACT

The present invention relates to a body support pillow made and contoured to promote side lying to reduce snoring and negate the consequences of sleep apnea and symptoms. It consists of a body support pillow with integrated, semi-rigid yet flexible support for a person's head, back, and legs while lying on their side thereby encouraging either left or right side position sleeping.

19 Claims, 5 Drawing Sheets

THERAPEUTIC POSITIONING DEVICE

FIELD OF THE INVENTION

The present invention relates generally to the field of reduction of snoring and sleep apnea back pain, osteoarthritis, and health and safety issues related to resting positioning through the avoidance of either supine or prone position sleeping. This invention relates to pillows, specifically to a body support pillow with integrated and semi-rigid yet flexible support for a person's head, back, and legs while lying on their side thereby encouraging either left or right side position sleeping.

BACKGROUND OF THE INVENTION

Numerous techniques have been developed previously by way of efforts to discourage supine or prone position sleeping. They include the positioning of uncomfortable objects in the area of the back such as by having a tennis ball sewn into a person's pajama top, or by tying a tennis ball to a person's back by straps or belt. In addition, early pillows served to prop up the head when a person would sleep or to serve as a supporting bolster for other parts of the body, such as the torso or legs. the recognition of the pillow as an important body support has persisted over the years. Recent studies of body ergonomics and renewed attention to the benefits of quality rest and sleep have, in fact, highlighted the utilitarian function of supportive pillows.

The pillows of U.S. Pat. No. 5,987,674, and U.S. Pat. No. 6,874,183 represent recent body pillows that provide integrated support to the head, back and legs of a user but fail provide direct support to the back in a manner that positively encourages a side-lying position. The pillow of U.S. Pat. No. 6,874,183 aims to provide support for a user in a wide range of positions and consequently is neither shaped or sufficiently semi-rigid to provide positive support that encourages the beneficial side-lying position. The pillow of U.S. Pat. No. 5,987,674 requires the user to embrace the pillow to achieve support and thus like many such pillows require the user to embrace the pillow, thereby blocking the ventral side of the body and frustrating the dissipation of heat by the body.

SUMMARY OF THE INVENTION

The invention is an integrated body support pillow that encourages side sleeping by urging a user to rest and sleep on their side, with a pillow section for the head, a pillow section for leg support and a connecting back support pillow, integrated into a pillow for the body.

The invention is a simple solution to structural obstructive sleep apnea that assists in the reduction of apnea events associated with either supine or prone sleep positions or unrestricted sleep, aids in reducing snoring, aids in alleviating back pain and reducing hip pain, reduces restless leg syndrome and ameliorates the pain of osteoarthritis. The use of the invention body support pillow encourages side lying, by urging a user to rest and sleep on their side, to promote better, more restful sleep and reduces apnea events associated with a supine or prone sleep position. It operates to position and then maintain a user in a side lying position for rest or sleep. It also aids in reducing snoring, and the consequent disruptive effects on others commonly associated with snoring. It also aids in alleviating lower back pain and reducing hip pain, reduces restless leg syndrome and ameliorates the pain of osteoarthritis. The invention body support pillow may be used in conjunction with other therapies, treatments, apparatus or surgery aimed at treating sleep apnea. When used alone as a therapeutic device the negative aspects, discomfort and potential health risks associated with other therapies are avoided. Such alternate therapies include dental appliances, CPAP machines, surgery, etc. It is a device that is portable, and superior to other products for encouraging side sleeping. It also reduces the risks associated with individuals who have difficulty breathing or who may be at risk of vomiting or having their windpipe close in their sleep.

The connection of neck, back and leg supports into an integrated body support pillow when used encourages side sleep by urging a user to rest and sleep on their side, and thereby positioning and maintaining a user in a side lying position for rest or sleep and reducing roll over to either supine or prone sleeping.

This invention consists of an integrated body support pillow for use by an adult or child. It is capable of providing a person with head, back and leg support in a manner that encourages slide sleeping on either the left or right side while allowing for movement of the head, arms, and legs.

In addition to encouraging side sleeping, the integrated body support pillow of the invention eliminates the need for more than one pillow to support the head, back and legs and can directly support the head, back and legs during side lying in a way that allows the front of the body to be free of obstruction.

In use, it can support the thighs, knees, legs, ankles, and feet in normal anatomical relation while it can maintain normal position for the joints of the hips, knees and ankles. It can allow for varied flexion of both at the hip and the knees and also separate the pressure points of the knees and ankles.

In another embodiment, the body support pillow is made so as to be folded in two for further ease of storage or transport.

Of course, the body support pillow, like any pillow, can have a number of variable internal chambers, or other means in order to control the movement of the compressible material within the casing. In turn, the compressible material can be made of various materials depending on the degree of desired support ranging for example, from natural fibre or synthetic fibre, foam, or down, or combinations, or even air or other fluids provided suitable casing is used. The body support pillow also could be covered with various types of fabric, so as to enhance durability, texture, comfort, and even aesthetic appeal. The body support pillow could also include a removable, washable slipcover over the casing.

Further objects and advantages of the body support pillow will become apparent from a consideration of the drawings and ensuing description.

BRIEF DESCRIPTION OF THE DRAWINGS

The present invention may be further understood by reference to the following detailed description of the embodiments of the invention, taken in conjunction with the accompanying drawings, in which.

DETAILED DESCRIPTION OF THE INVENTION

Figure 1:
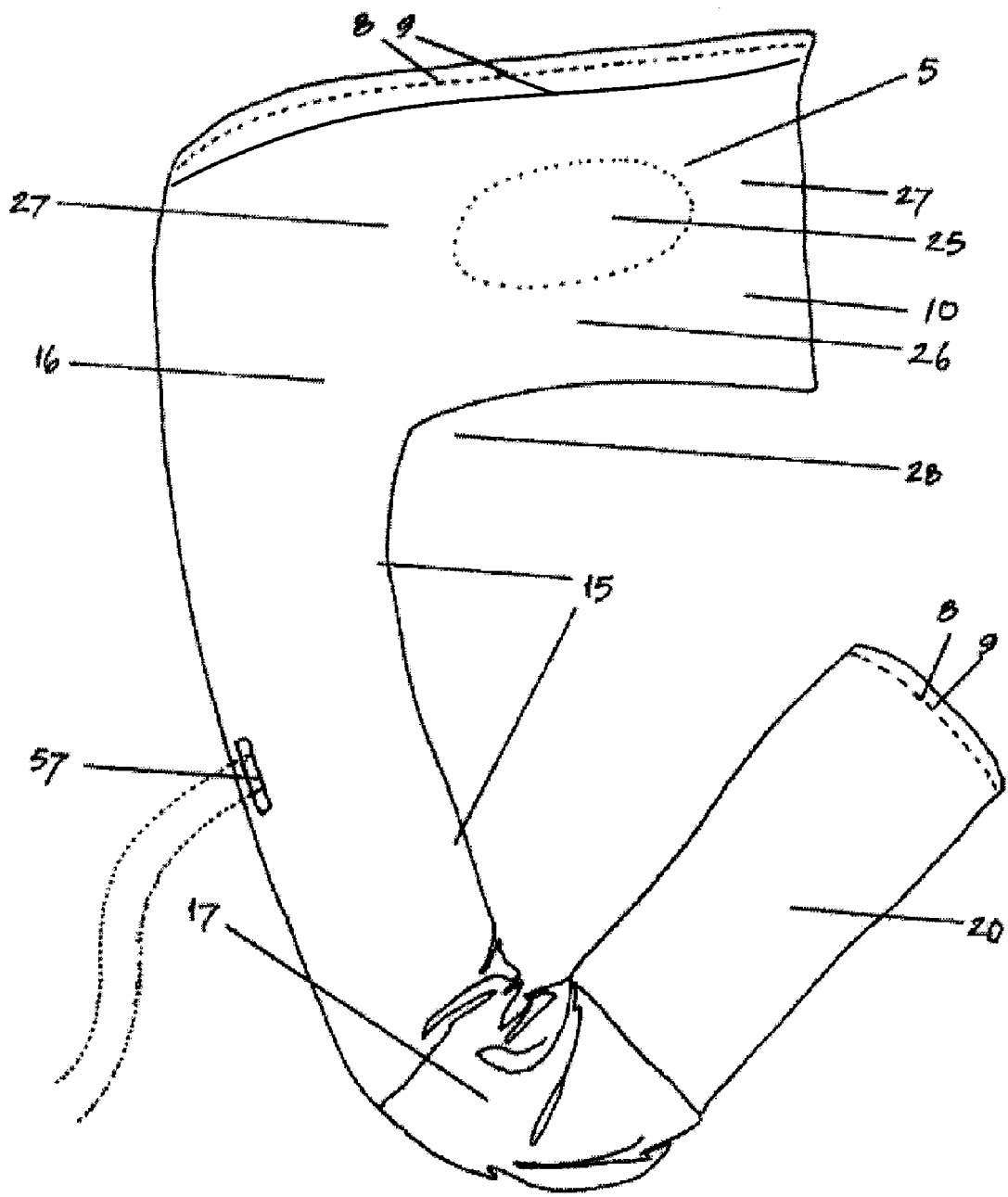
FIG. 1 (hereafter FIG. 1) shows a left side elevation view of an embodiment of the body support pillow.

The description, which follows, and the embodiment described therein, are provided by way of illustration of an example, or examples of particular embodiments of principles and aspects of the present invention. These examples are provided for the purposes of explanation, and not of limitation, of those principles and of the invention. In the description that follows, like parts are marked throughout the specification and the drawings with the same respective reference numerals.

Figure 2:
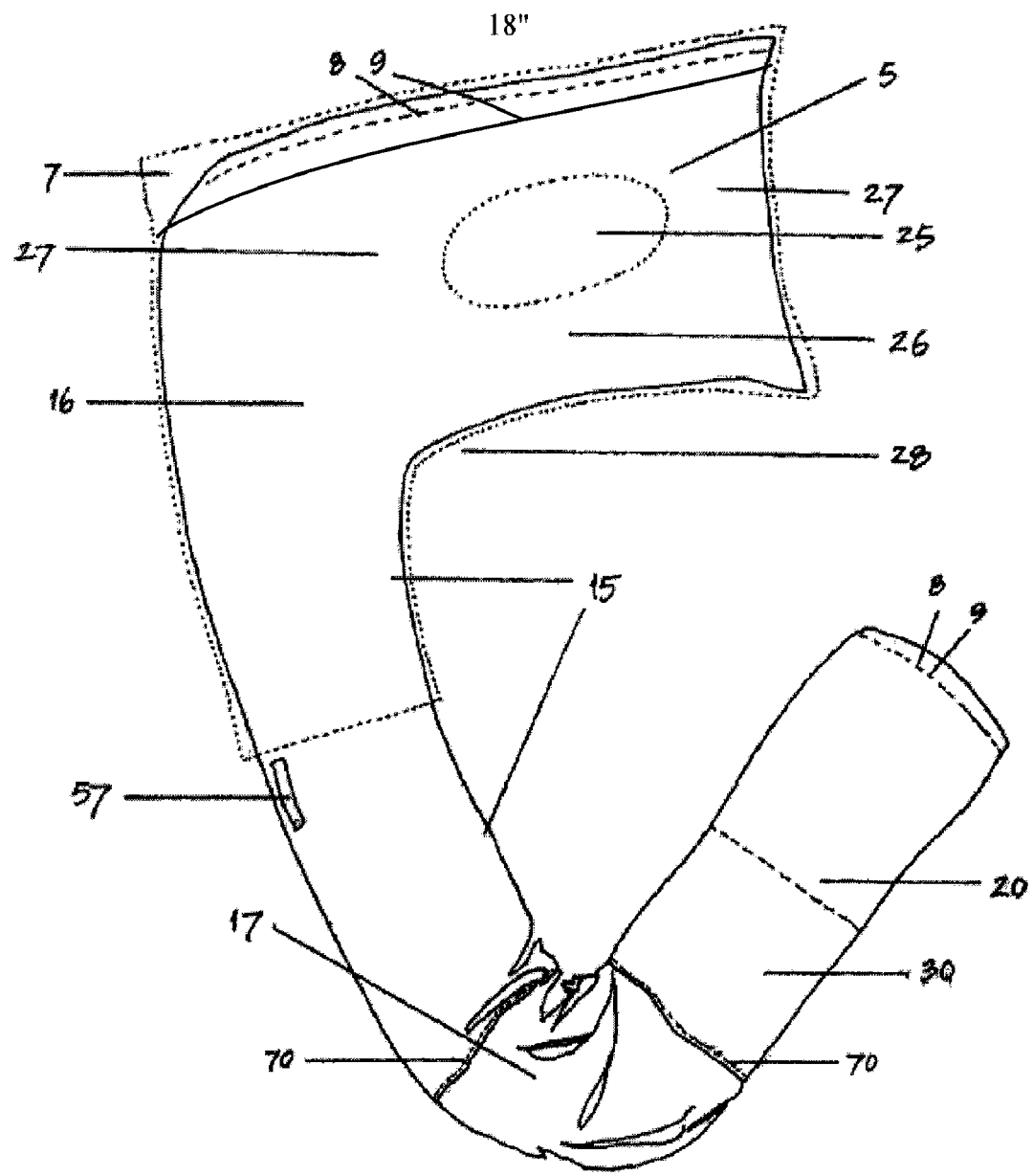
FIG. 2 (hereafter FIG. 2) shows a side elevation view of the body support pillow, corresponding to the left side of another embodiment of the body support pillow.

FIG. 1 and FIG. 2 show views of basic versions of the body support pillow according to the invention. The pillow 5 is an integrated, semi-rigid yet flexible, resilient and contoured article having a distinctive shape. The body support pillow 5 structure comprises a substantially block-shaped head support section 10 and a leg support section 20, which are joined by a substantially straight elongate substantially block-shaped back section 15 comprising two portions namely, main portion 16 and length portion 17. The head support section 10 is joined perpendicularly to the back support section 15 and the leg support section 20 is joined perpendicularly to a forward angled length portion 17 of the back support section 15 in a manner so as to create an elongated C-shaped contour overall. Alternatively, the back support section can comprise one or more portions with a straight alignment having no forward angled length portion. The cross-sectional shape of each of these three sections 10, 15, and 20 is generally rectangular in nature, and consist of a fabric case 7 with openings 8 having covering flaps 9, as shown in FIG. 1 and FIG. 2, encasing materials of varying degrees of compressibility.

Figure 3:
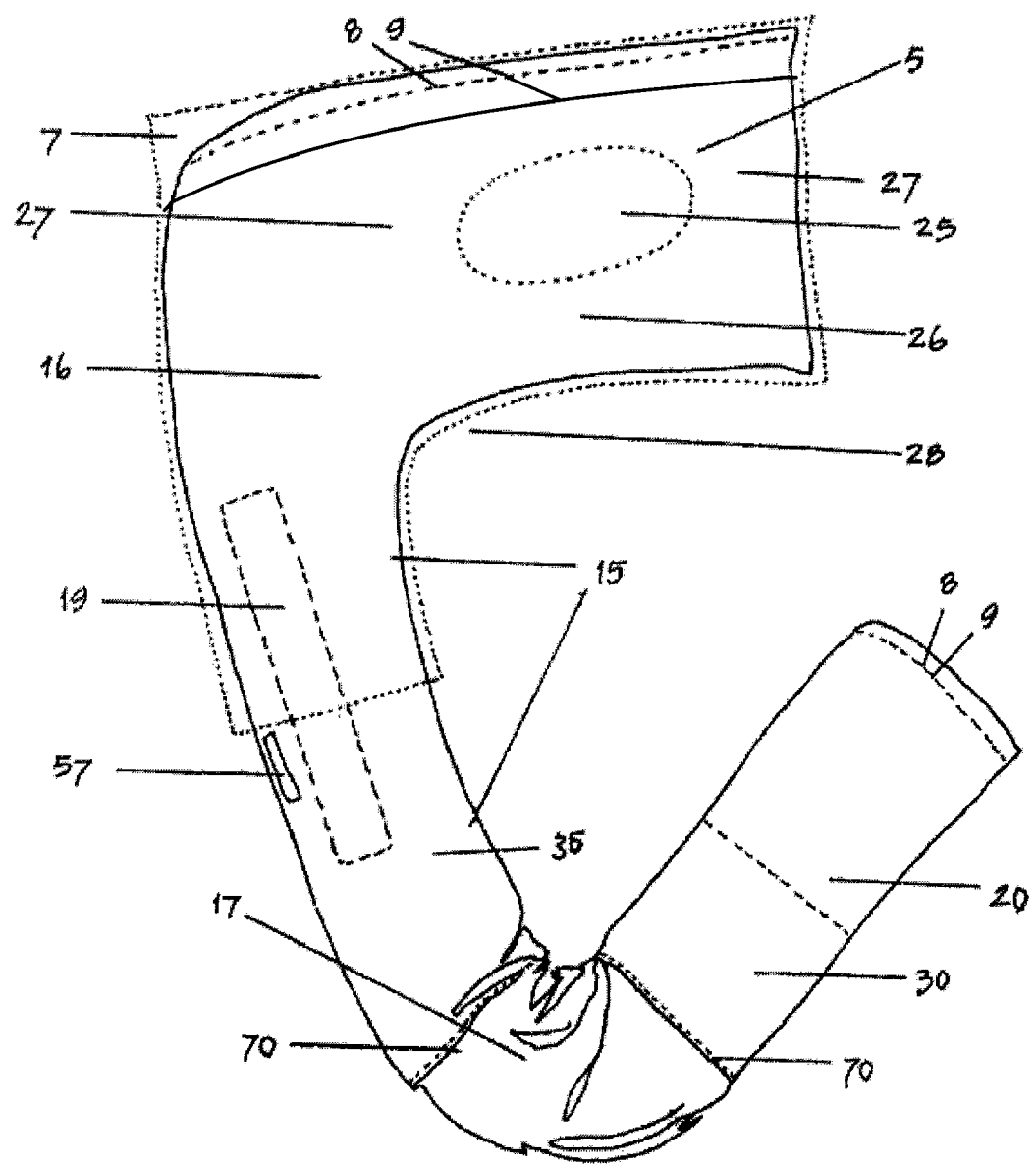
FIG. 3 (hereafter FIG. 3) shows a side elevation view of the body support pillow, corresponding to the left side of a further embodiment of the body support pillow.

As may be noted in FIG. 2 and FIG. 3, the head support section 10 generally terminates in a somewhat enlarged end, zone 27. Each side of the head support section 10 incorporates portions, zones 25, that can each accommodate the side of a person's head with shallow compressible indentations. These zones 25 are made of compressible material, located substantially at midpoint on both the left and right sides of the section, each located substantially three-quarters of the way down from the top of the section, having a substantially oval shape, each having a depth of about one inch and compressible to a further depth of about one inch and having a width of about six inches. The portions of the section beneath and adjacent the zones 25 and extending to the bottom of the section, consist of another zone 26, that can accommodate a person's neck by forming shallower indentations. These zones 26 are made of material compressible to a depth of about one inch and having a width of about six inches. The remaining portions of the section, zones 27, sandwich zones 25 and zones 26 and are made of material firmer than the respective compressible material of zones 25 and zones 26. Alternately, zones 25 can be flush with the adjoining zones 27 and made of material compressible to a depth of about two inches. Zones 26 are also contoured to create space 28 in order to accommodate the shoulder of a user.

As may be noted further in FIG. 2, the leg support section 20 alternatively incorporates portions, zones 30, made of compressible material that can accommodate a person's legs. These zones 30 are located substantially at midpoint on both the left and right sides of the section, each traversing the section from top to bottom, each compressible to a depth of about 2 inches and having a width of about six inches.

Of course, the dimensions of the body support pillow can be custom tailored to fit the frame of a particular user, or made to fit set categories of dimensions such as small, medium, tall, etc. Generally, the length of the body support pillow substantially corresponds to the height of the user. The head support section 10 is about eighteen inches along its top and the leg support section 20 is about twelve inches along its bottom. Zone 16 of the back section 15 is about four to five inches from back to front. Back section 15 has the same firmness as the zones 27.

To aid in the adjustment of the body support pillow, or in the handling, storage or transport of the body support pillow, an alternative embodiment allows head portion 10 and leg support section 20 to each be detachably secured to the back section 15 by suitable fastener means 70, such as zippers, buttons or VELCRO® fasteners, as shown in FIG. 2.

In a still further alternative embodiment, as shown in FIG. 3, back section 15 has a portion located at substantially midpoint, zone 35. Zone 35 is about one foot in length and made with sufficiently compressible material that it can act as a folding zone and permit the folding of the back section in two so that the upper portion of the back section may be placed onto the lower section or vice verse to aid in handling, storage or transport of the body support pillow.

Figure 4:
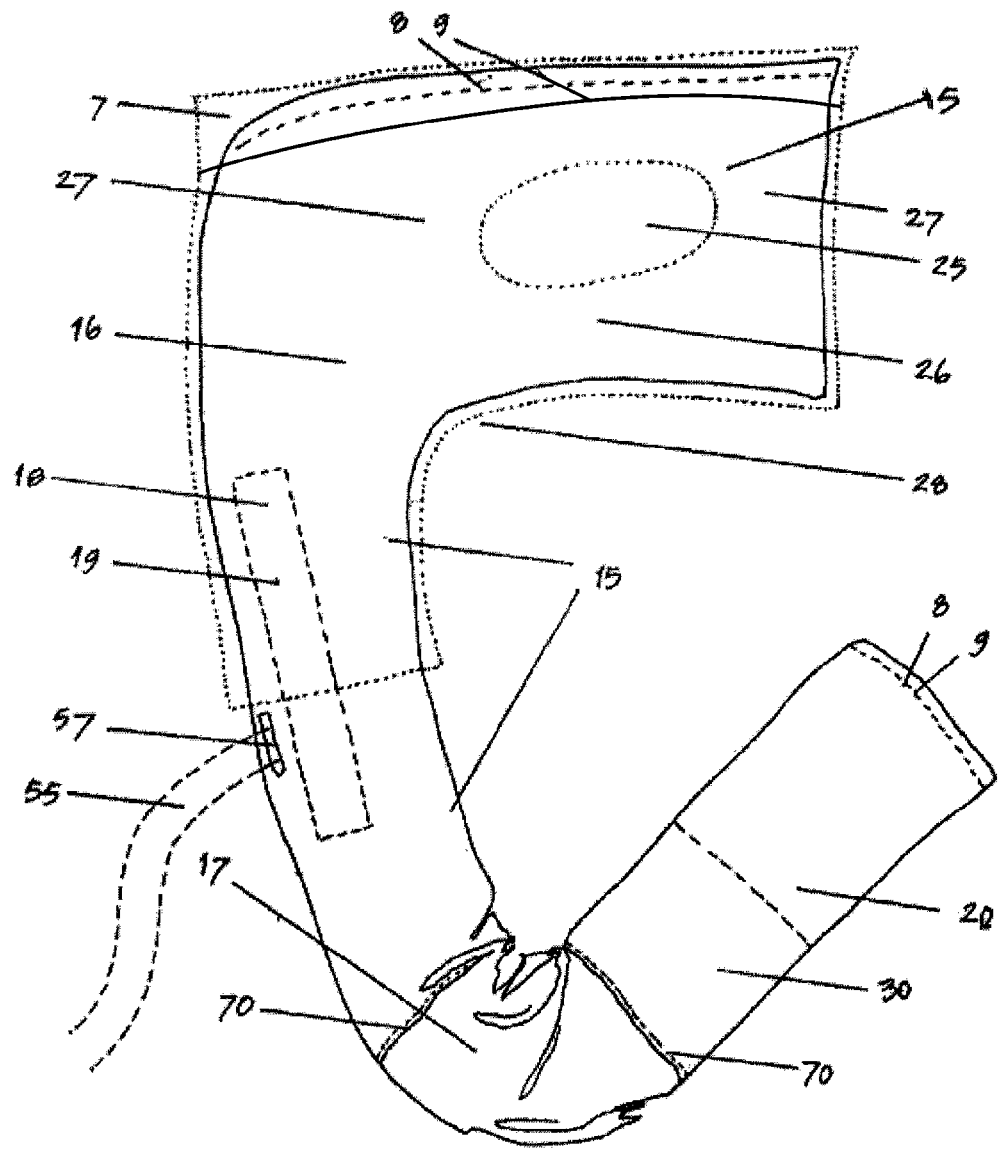
FIG. 4 (hereafter FIG. 4) shows a side elevation view of the body support pillow, corresponding to the left side of a still further embodiment of the body support pillow.
Figure 5:
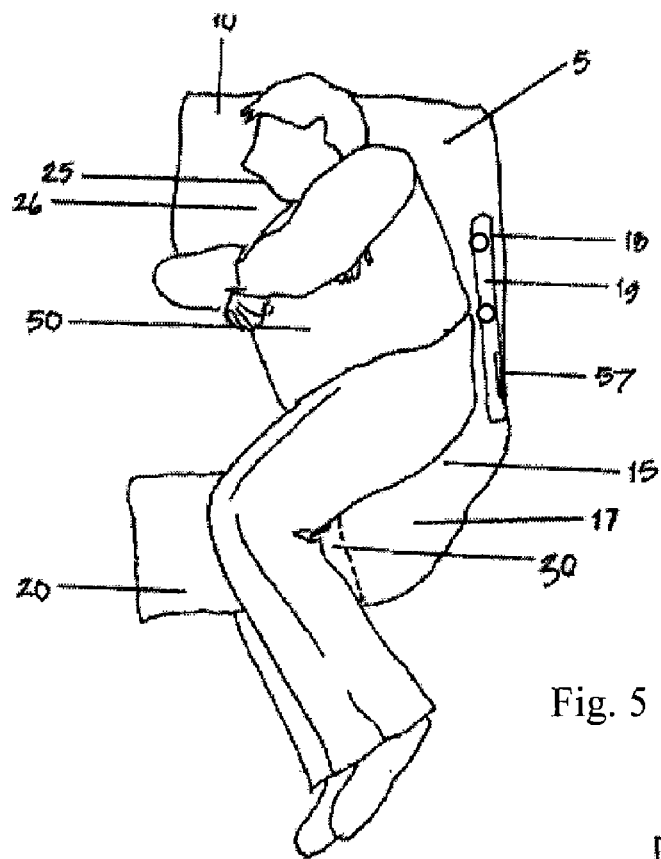
FIG. 5 (hereafter FIG. 5) shows a perspective view of an embodiment of the body support pillow as it supports a user in a side-lying position.
Figure 6:
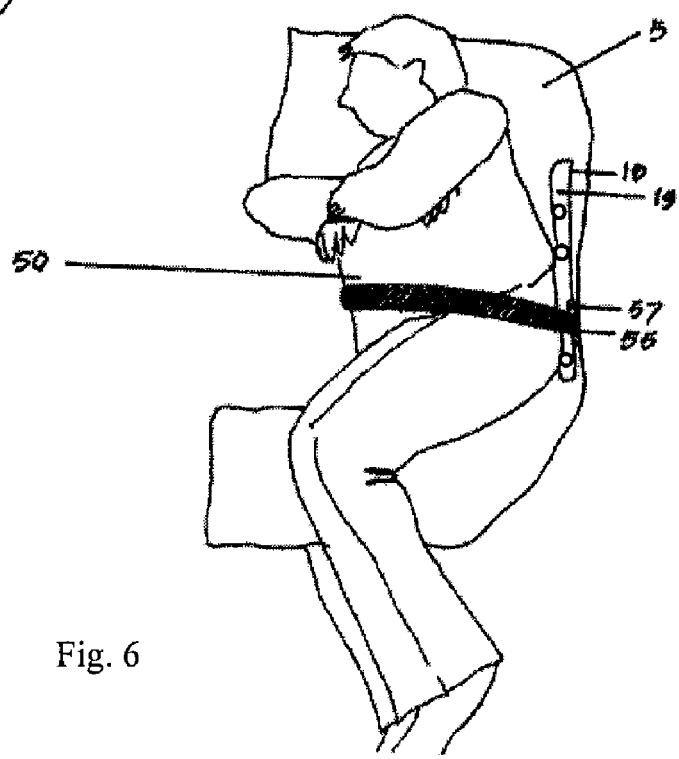
FIG. 6 (hereafter FIG. 6) shows a perspective view of the body support pillow of FIG. 5 as it supports the user using a body strap, in a side-lying position.

In a further alternative embodiment, back support section 15 incorporates means to discourage prone or supine resting or sleeping on the back support section. These means include a plurality of protrusions or a projecting ridge or ridges provided along the lengths of the left and right sides of the body support pillow to provide an uncomfortable surface on which to lie so as to inhibit a user from rolling over the body support pillow. The protrusions or projecting ridge can be provided, by embedding them within the back section 15, or, as shown in FIG. 4, by mounting them on the appropriate surface of the back section 15 by means of placing an insert 18 that has projecting ridges or protruding portions (as best seen in FIG. 5 and 6) within a suitable pocket 19 located on the appropriate surface of the back section 15. Thus if one lies on the back section 15 with such protrusions or ridges, it will be uncomfortable and will cause one to shift off it to the appropriate and comfortable side sleeping position.

The degree of desired firmness or support will influence the cross-sectional dimension of the three support sections and the compressible material chosen for the three different sections such as natural, synthetic or blended fibre. The height of the body support pillow ranges from six to eight inches, with the back support section 15 having somewhat greater height than the head support section 10 and the leg support section 20.

The case 7 encasing the compressible material of the body support pillow is formed by suitable panels of fabric joined together along seams by known methods of sewing or other means of joining panels, and with suitable openings 8, having covering flaps 9 fastened by suitable means (such as zippers, buttons, etc.) to facilitate the encasing of the body support pillow 5 as well as the removal of the case 7 for cleaning, mending or replacement.

As shown in FIG. 5, the principal manner of using the body support pillow as a body support is in a side-lying position of the user 50 which thereby encourages side sleeping. One side of the head support section 10 of the body fits under the head of the user 50, with the respective zone 25 providing a head rest and the respective zone 26 providing a neck rest, while the user 50's back is directly bolstered by the back support section 15. The leg support section 20 of the body support pillow 5 fits between the legs of the user 50, with zones 30 thus providing support between the thighs, legs, and feet. The substantially block shape of the sections of the body support pillow resists dislodgement of the body support pillow from the preferred side-lying operating attitude on the resting or sleeping platform by bodily movements of the user.

The body support pillow 5 also permits a range of motion for the head, arms and legs of the user while encouraging side sleeping. The zones 25 and 26 of the head support section 10 allow the user to adjust the position of the head while the arms are able to be positioned as in normal side sleeping. The leg support section 20 permits leg extension or bending with support of the ankles of user.

Use of the invention body support pillow encourages and enables a person to rest or sleep in a comfortable and anatomically natural side lying position on either the left side or the right side while discouraging supine or prone position sleeping. A user of the invention body support pillow obtains direct, integrated support to the head, back and legs during side lying while allowed varied, natural movement of the arms and legs of the user of the invention body support pillow.

In addition, the body support pillow can be fitted with means to fasten the body support pillow to the resting or sleeping platform in order to restrain the dislodgement of the body support pillow from the preferred side-lying operating attitude on the resting or sleeping platform, such as VELCRO fasteners or straps that cooperate with suitable harness on the resting or sleeping platform. In this regard, other means can be used to keep the body support pillow in its preferred attitude including weighting the side of the body support pillow to rest on the resting or sleeping platform or propping the body support pillow into its preferred attitude.

In an alternative embodiment, the body support pillow can be fitted with means to fasten the body support pillow to a user such as chest strap 55 held by belt straps 57, as shown in FIG. 1 and FIG. 4 and FIG. 6.

In an alternative embodiment, the body support pillow has means to provide heat to the different support sections of the invention body support pillow such as pockets in the casings to hold hot water bottles in order to aid in alleviating muscle ache or pain or strain, restless leg syndrome, the ache of arthritis, promote increased circulation, and further encourage relaxation and restful sleep.

In an alternative embodiment, the body support pillow has means to provide sound (or music), massage, vibration, sources of scents or aromas, and/or heat to the different support sections of the invention body support pillow such as pockets in the casings to hold hot water bottles in order to aid in alleviating muscle ache or pain or strain, restless leg syndrome, the ache of arthritis, promote increased circulation, and further encourage relaxation and restful sleep.

In an alternative embodiment, the body support pillow has means to sense certain physical functions of the user, such as breathing effort, respiratory effort, respiratory events, apnea or hyponea events, brain or neural activity, snoring event, snoring sound intensity, vibrations or movement in limbs, temperature, blood pressure, pulse rate, and oxygen and $CO_2$ saturation levels in the user. These means can include heart rate monitors, blood pressure monitors, electroencephalography, neural sensors, physical sensors, eye movement sensors, nasal or mouth breathing sensors, blood composition sensors, muscle sensors, or other polysomnographic sensors.

In an alternative embodiment, the body support pillow has means to record the sensors or display results of the sensors to others or the user.

In an alternative embodiment, the body support pillow has means to monitor the user and allow self-assessment, third-party or professional assessment, such by means of a physical, telecommunication or internet system, which may relay the sensed results of the user whereby they are forwarded on to a medical site, or computerized medical center to allow for consistent, intermittent or alarm-based medical monitoring. For example in the event that the users sleep apnea creates dangerously low oxygen levels or the user's detected recordings indicates they are suffering from a serious medical condition, such as heart attack or stroke, the sensing and diagnostic system may contact emergency or non-emergency medical services.

Although the invention has been variously called invention body support pillow, integrated body support pillow and body support pillow and described for illustrative purpose with reference to particular shapes, processes, and materials, these should not be construed as limiting the scope of the present invention. It will be understood that various changes, modifications and adaptations may be made without departing from the spirit of the invention.

The embodiments of the invention in which an exclusive property or privilege is claimed are defined as follows:

1. An integrated, semi-rigid yet flexible, resilient body support pillow of compressible material, conforming substantially to a user's bodily skeletal dimensions, comprising:
  a. a block-shaped head support section, having a proximate end and a distal end,
  b. a block-shaped leg support section, having a proximate end and a distal end, and
  c. an elongate, block-shaped back support section with a substantially straight alignment comprising one or more joined portions connected substantially perpendicularly at a first end to said proximate end of said head support section to form an L-shaped semi-rigid, yet flexible and resilient support, and connected at a second end of said back support section to said proximate end of said leg support section, wherein:
  said head support section comprises a shallow indentation comprising a first compressible material, wherein said indentation is capable of accommodating a side of said user's head,
  said back support portion comprises a second compressible material that is firmer than said first compressible material in said shallow indentation,
  said pillow is shaped so that a head, back, and legs of said user are simultaneously and flexibly supported by said pillow when said user is in a side-lying position,
  said pillow allows for a range of user body motion, and substantially all of said user's front chest and abdomen remains unobstructed by said pillow when said user is in said side-lying position, thereby promoting side-lying sleeping while discouraging prone or supine sleeping.

2. A body support pillow according to claim 1, wherein said back support section comprises two joined portions, namely, a main portion, which is substantially straight, and a length portion, which angles forward.

3. A body support pillow according to claim 1, further incorporating on each head support surface sides of said head support section, a shallow, compressible neck indentation, which is capable of accommodating said user's neck, and which is located below said indentation and contoured to define a free space capable of accommodating a shoulder of said user.

4. A body support pillow according to claim 1, wherein said leg support section incorporates on each side a compressible portion capable of accommodating a user's legs, located substantially at midpoint on the respective side of said leg support section, and traversing said leg support section from top to bottom.

5. A body support pillow according to claim 1, incorporating means with the back support section to further discourage prone or supine sleeping.

6. A body support pillow according to claim 5, wherein said means to discourage prone or supine sleeping comprise one or more protrusion provided along the length of one or more of the sides of said back support section to provide an uncomfortable surface on which to lie so as to inhibit a user from rolling over the body support pillow.

7. A body support pillow according to claim 1, further including a casing, said casing conforming to the shape of said pillow, made of durable, washable fabric, with openings having covering flaps to facilitate the encasing of said body support pillow as well as the removable of the casing for cleaning, mending or replacement.

8. A body support pillow according to claim 1, further incorporating means to detachably secure said body support pillow to the sleeping platform in order to prevent dislodgement of said body support pillow from preferred side-lying attitude on said sleeping platform.

9. A body support pillow according to claim 1, incorporating means to provide heat to one or more of said support sections of said body support pillow, in order to aid in alleviating muscle ache or pain or strain, or restless leg syndrome, or ache of arthritis, promote increased circulation, and further encourage relaxation and restful sleep, for said user.

10. A body support pillow according to claim 1, wherein said back support section is sufficiently compressible at a joint between said main portion and said length portion to permit said back support section to fold such that said main portion is placed onto said length section to aid handling, storage or transport of said body support pillow.

11. A body support pillow according to claim 10, wherein said back support section is detachably secured to said leg support section, to further aid in the adjustment of said body support pillow, and in the handling, storage or transport of said body support pillow.

12. A body support pillow according to claim 1, having an internal chamber to restrain movement of said compressible materials within said body support pillow.

13. A body support pillow according to claim 12, wherein said internal chamber comprises two or more internal chambers.

14. A body support pillow according to claim 1, incorporating means to provide one or more of sounds, vibration, or aromas to the different support sections of said body support pillow to further encourage relaxation and restful sleep.

15. A body support pillow according to claim 1, incorporating means to sense one or more physical function of said user including breathing effort, respiratory effort, respiratory events, apnea events, hyponea events, brain or neural activity, snoring events, snoring sound intensity, vibrations or movement in limbs, temperature, blood pressure, pulse rate, and oxygen and CO2 saturation levels in said user.

16. A body support pillow according to claim 15, incorporating means to record results sensed by said sensors.

17. A body support pillow according to claim 15, having means to monitor said physical functions of said user and assessment by others by communication of said sensed results to others including medical services personnel to allow for medical monitoring of said functions of said user.

18. An integrated, semi-rigid yet flexible, resilient body support pillow of compressible material, conforming substantially to a user's bodily skeletal dimensions, comprising:

a. a block-shaped, substantially rectangular, head support section, having a proximate end and a distal end, b. an elongate, block-shaped leg support section, having a proximate end and a distal end, and c. an elongate, block-shaped back support section comprising a main portion and a length portion, wherein:

said main portion comprises a substantially straight alignment, a first end of said main portion is connected substantially perpendicularly to said proximate end of said head support section to form an L-shaped semi-rigid yet flexible, resilient support, said length portion hingedly connects said elongate leg portion to a second end of said main portion, said head support section comprises a shallow indentation comprising a first compressible material, wherein said indentation is capable of accommodating a side of said user's head.

said back support portion comprises a second compressible material that is firmer than said first compressible material in said shallow indentation, said head support section farther comprises a neck support zone disposed below said shallow indentation and contoured to define a free space capable of accommodating a shoulder of the user, said elongate leg support portion incorporates on each side a compressible portion capable of accommodating said user's legs, said pillow is shaped so that a head, back, and legs of said are simultaneously and flexibly supported by said pillow when said user is in a side-lying position, and said pillow allows for a range of user body motion, and said user's front chest and abdomen remains unobstructed by said pillow when said user is in said side-lying position, thereby promoting side-lying sleeping while discouraging prone or supine sleeping.

19. An integrated, semi-rigid yet flexible, resilient body support pillow of compressible material, conforming substantially to a user's bodily skeletal dimensions, comprising:

a. a block-shaped, head support section, having a proximate end and a distal end, b. an elongate, block-shaped back support section comprising a main portion and a length portion, and c. an elongate, block-shaped leg support section having a proximate end and a distal end, wherein:

a first end of said main portion is connected substantially perpendicularly to said proximate end of said head support section to form an L-shaped semi-rigid yet flexible, resilient support, said elongate leg support section comprises a portion of said compressible material that is separate and discrete from said compressible material used in said head support section and said back support section, said leg support section being hingedly and detached secured to said back support section;

said pillow is shaped so that a head, back, and legs of said are simultaneously and flexibly supported by said pillow when said user is in a side-lying position, said pillow allows for a range of user body motion, and said user's front chest and abdomen remains unobstructed by said pillow when said user is in said side-lying position, thereby promoting side-lying sleeping while discouraging prone or supine sleeping.

* * * * *